United States Patent
Potter (10) Patent No.: US 12,213,537 B2
(45) Date of Patent: Feb. 4, 2025

(54) MOUTHPIECE ASSEMBLY

(71) Applicant: NICOVENTURES TRADING LIMITED, London (GB)

(72) Inventor: Mark Potter, London (GB)

(73) Assignee: NICOVENTURES TRADING LIMITED, London (GB)

( * ) Notice: Subject to any disclaimer, the term of this patent is extended or adjusted under 35 U.S.C. 154(b) by 147 days.

(21) Appl. No.: 16/758,979

(22) PCT Filed: Oct. 24, 2018

(86) PCT No.: PCT/EP2018/079137
§ 371 (c)(1),
(2) Date: Apr. 24, 2020

(87) PCT Pub. No.: WO2019/081569
PCT Pub. Date: May 2, 2019

(65) Prior Publication Data
US 2020/0288770 A1   Sep. 17, 2020

(30) Foreign Application Priority Data

Oct. 24, 2017   (GB) .................................. 1717497

(51) Int. Cl.
*A24F 7/02* (2006.01)
*A24F 40/10* (2020.01)
(Continued)

(52) U.S. Cl.
CPC ............... *A24F 7/02* (2013.01); *A24F 40/30* (2020.01); *A24F 40/40* (2020.01); *A24F 40/70* (2020.01);
(Continued)

(58) Field of Classification Search
CPC .......... A24F 40/10; A24F 40/485; A24F 7/04; A24F 7/02; A24F 40/40
See application file for complete search history.

(56) References Cited

U.S. PATENT DOCUMENTS 4,790,332 A * 12/1988 Wallace ................. A24F 13/18
131/330
4,911,181 A    3/1990 Vromen
(Continued)

FOREIGN PATENT DOCUMENTS

CA       3010559 A1    7/2017
CL    2017003355 A1    6/2018
(Continued)

OTHER PUBLICATIONS

International Search Report and Written Opinion, Application No. PCT/EP2018/079137, mailed Jan. 31, 2019, 2 pages.
(Continued)

*Primary Examiner* — Michael H. Wilson
*Assistant Examiner* — Stephanie Lynn Moore
(74) *Attorney, Agent, or Firm* — Husch Blackwell (57) ABSTRACT

A mouthpiece assembly for an aerosol provision device includes a first housing for being received, in use, in a mouth of a user, and a second housing for containing a material through which, in use, an aerosol generated by the aerosol provision device flows before passing out of the mouthpiece assembly for inhalation by the user. The first housing and the second housing are connected together to form the mouthpiece assembly, and the mouthpiece assembly is configured to be releasably connectable to a section of the aerosol provision device.

27 Claims, 7 Drawing Sheets

(51) Int. Cl.
   *A24F 40/20*      (2020.01)
   *A24F 40/30*      (2020.01)
   *A24F 40/40*      (2020.01)
   *A24F 40/485*     (2020.01)
   *A24F 40/70*      (2020.01)

(52) U.S. Cl.
   CPC ............... *A24F 40/10* (2020.01); *A24F 40/20* (2020.01); *A24F 40/485* (2020.01)

(56) References Cited

U.S. PATENT DOCUMENTS

| | | | |
|---|---|---|---|
| 5,135,009 | A | 8/1992 | Muller |
| 5,880,439 | A | 3/1999 | Deevi et al. |
| 7,278,283 | B2 | 10/2007 | Meckbach |
| 9,004,073 | B2 | 4/2015 | Tucker |
| 9,101,729 | B2 | 8/2015 | Liu |
| 9,462,830 | B2 | 10/2016 | Liu |
| 10,375,996 | B2 | 8/2019 | Aoun et al. |
| 10,842,189 | B1 | 11/2020 | Hermiz et al. |
| 11,129,413 | B2 | 9/2021 | Lipowicz et al. |
| 11,229,758 | B2 | 1/2022 | Davidson et al. |
| 11,259,758 | B2 | 3/2022 | Modai et al. |
| 2007/0102013 | A1 | 5/2007 | Adams |
| 2008/0276948 | A1 | 11/2008 | Gedevanishvili |
| 2013/0014772 | A1 | 1/2013 | Liu |
| 2013/0074857 | A1 | 3/2013 | Buchberger |
| 2013/0319407 | A1 | 12/2013 | Liu |
| 2013/0333700 | A1 | 12/2013 | Buchberger |
| 2014/0000638 | A1 | 1/2014 | Sebastian et al. |
| 2014/0041655 | A1* | 2/2014 | Barron ................... A24F 40/46 128/202.21 |
| 2014/0166029 | A1 | 6/2014 | Weigensberg et al. |
| 2014/0314397 | A1 | 10/2014 | Alima |
| 2015/0374039 | A1 | 12/2015 | Zhu |
| 2016/0015081 | A1 | 1/2016 | Liu |
| 2016/0106153 | A1 | 4/2016 | Zhu |
| 2016/0135505 | A1 | 5/2016 | Li et al. |
| 2016/0135506 | A1 | 5/2016 | Sanchez et al. |
| 2016/0178377 | A1 | 6/2016 | Jung et al. |
| 2016/0192713 | A1 | 7/2016 | Memari et al. |
| 2016/0262449 | A1 | 9/2016 | Liu |
| 2016/0262452 | A1 | 9/2016 | Zhu |
| 2016/0270438 | A1 | 9/2016 | Jackson et al. |
| 2016/0295919 | A1 | 10/2016 | Thomas, Jr. |
| 2016/0324216 | A1 | 11/2016 | Li et al. |
| 2016/0345626 | A1* | 12/2016 | Wong ..................... A24F 40/90 |
| 2016/0366941 | A1 | 12/2016 | Lin |
| 2017/0035117 | A1 | 2/2017 | Lin |
| 2017/0042252 | A1* | 2/2017 | Takeuchi ................. A24F 40/53 |
| 2017/0238606 | A1 | 8/2017 | Matsumoto et al. |
| 2017/0238614 | A1 | 8/2017 | Li |
| 2019/0001087 | A1 | 1/2019 | Davidson et al. |
| 2019/0053544 | A1* | 2/2019 | Yamada ................. A24F 40/485 |
| 2019/0142069 | A1 | 5/2019 | Qiu |
| 2020/0324066 | A1 | 10/2020 | Potter |
| 2020/0350736 | A1 | 11/2020 | Jung et al. |
| 2020/0383379 | A1 | 12/2020 | Yilmaz |
| 2021/0030981 | A1 | 2/2021 | Azzopardi et al. |
| 2021/0329976 | A1 | 10/2021 | Nelson et al. |

FOREIGN PATENT DOCUMENTS

| | | | |
|---|---|---|---|
| CL | 2018002292 A1 | 12/2018 | |
| CL | 2018003164 A1 | 2/2019 | |
| CL | 2018003426 A1 | 3/2019 | |
| CL | 2019001317 A1 | 8/2019 | |
| CL | 2019001161 A1 | 9/2019 | |
| CL | 2019002751 A1 | 2/2020 | |
| CN | 201294864 | 8/2009 | |
| CN | 201591126 | 9/2010 | |
| CN | 103844359 A | 6/2014 | |
| CN | 203748680 U | 8/2014 | |
| CN | 203986126 U | 12/2014 | |
| CN | 204217898 U | 3/2015 | |
| CN | 204466908 U | 7/2015 | |
| CN | 104886776 A | 9/2015 | |
| CN | 105768225 A | 7/2016 | |
| CN | 106037011 A | 10/2016 | |
| CN | 106136332 A | 11/2016 | |
| CN | 106858725 A | 6/2017 | |
| CN | 106880085 | 6/2017 | |
| CN | 107048479 A | 8/2017 | |
| CN | 108926037 A | 12/2018 | |
| EA | 201290392 A1 | 10/2012 | |
| EA | 201270596 A1 | 11/2012 | |
| EP | 1867357 A1 | 12/2007 | |
| EP | 2732713 A1 | 5/2014 | |
| EP | 2989912 A1 | 3/2016 | |
| EP | 3039976 A1 | 7/2016 | |
| EP | 3135139 A1 | 3/2017 | |
| GB | 2497536 | 6/2013 | |
| JP | 2013521074 A | 6/2013 | |
| JP | 3211213 U | 6/2017 | |
| KR | 20090077899 A | 7/2009 | |
| KR | 101552254 | 9/2015 | |
| KR | 1020160044712 A | 4/2016 | |
| KR | 20170073664 A | 6/2017 | |
| RU | 103281 U1 | 4/2011 | |
| RU | 2014117968 A | 11/2015 | |
| RU | 2604313 C2 | 12/2016 | |
| RU | 2606072 C2 | 1/2017 | |
| RU | 2616556 C2 | 4/2017 | |
| RU | 2631623 C2 | 9/2017 | |
| RU | 2692497 C1 | 6/2019 | |
| WO | WO 2009043202 | 4/2009 | |
| WO | WO-2011050943 A1 | 5/2011 | |
| WO | WO-2011063970 A1 | 6/2011 | |
| WO | WO 2012106739 | 8/2012 | |
| WO | WO-2013000967 A1 | 1/2013 | |
| WO | WO-2013050934 A1 | 4/2013 | |
| WO | WO-2013118299 A1 | 8/2013 | |
| WO | WO-2014004648 A1 | 1/2014 | |
| WO | WO-2014116974 A1 | 7/2014 | |
| WO | WO-2014201432 A1 | 12/2014 | |
| WO | WO-2015179388 A1 | 11/2015 | |
| WO | WO-2016054580 A1 | 4/2016 | |
| WO | WO-2016062777 A1 | 4/2016 | |
| WO | WO-2016076176 A1 | 5/2016 | |
| WO | WO-2016090426 A1 | 6/2016 | |
| WO | WO-2016107768 A1 | 7/2016 | |
| WO | WO 2016121143 | 8/2016 | |
| WO | WO-2016135342 A2 | 9/2016 | |
| WO | WO-2016178377 A1 | 11/2016 | |
| WO | WO-2016184824 A1 | 11/2016 | |
| WO | WO-2016207407 A1 | 12/2016 | |
| WO | WO-2017001818 A1 | 1/2017 | |
| WO | WO-2017064324 A1 | 4/2017 | |
| WO | WO-2017093357 A1 | 6/2017 | |
| WO | WO-2017122196 A1 | 7/2017 | |
| WO | WO-2017139662 A1 | 8/2017 | |
| WO | WO-2017141358 A1 | 8/2017 | |
| WO | WO-2017149154 A1 | 9/2017 | |
| WO | WO-2017187545 A1 * | 11/2017 | ............ A24F 40/42 |
| WO | WO-2017194763 A2 | 11/2017 | |
| WO | WO-2017194766 A1 | 11/2017 | |
| WO | WO-2017216516 A1 | 12/2017 | |
| WO | WO-2018020599 A1 | 2/2018 | |
| WO | WO-2018083037 A1 | 5/2018 | |
| WO | WO-2018100366 A2 | 6/2018 | |
| WO | WO-2018141466 A1 | 8/2018 | |
| WO | WO-2018178900 A1 | 10/2018 | |
| WO | WO-2018206697 A2 | 11/2018 | |
| WO | WO-2019081571 A1 | 5/2019 | |
| WO | WO-2019081897 A1 | 5/2019 | |
| WO | 2022248708 A1 | 12/2022 | |

OTHER PUBLICATIONS

International Preliminary Report on Patentability, Application No. PCT/EP2018/079137, mailed Mar. 26, 2020, 6 pages.
Communication for the EP application. 18803870.7 mailed on Apr. 28, 2020, 4 pages.

(56) References Cited

OTHER PUBLICATIONS

Decision of Refusal mailed Jan. 18, 2022 for Japanese Application No. 2020-526244, 8 pages.
Extended European Search Report for Application No. 19216390.5, mailed on Mar. 26, 2020, 8 pages.
International Preliminary Report on Patentability for Application No. PCT/EP2018/079136, mailed on Feb. 5, 2020, 8 pages.
International Preliminary Report on Patentability for Application No. PCT/EP2018/079139, mailed on May 7, 2020, 8 pages.
International Preliminary Report on Patentability for Application No. PCT/EP2018/082411, mailed on Jun. 4, 2020, 7 pages.
International Search Report and Written Opinion for Application No. PCT/EP2018/079139, mailed on Mar. 14, 2019, 09 pages.
International Search Report for Application No. PCT/EP2018/079136, mailed on Feb. 12, 2019, 5 pages.
International Search Report for Application No. PCT/EP2018/082411, mailed on Mar. 22, 2019, 3 pages.
Korean Office Action mailed Feb. 6, 2020 for Korean Application No. 10-2019-7027109, 15 pages.
Notice of Acceptance mailed Jun. 2, 2021 for Australian Patent Application No. 2018355717, 3 pages.
Notice of Allowance for Korean Application No. 10-2019-7027109, dated Jan. 22, 2021, 5 pages.
Notice of Reasons for Refusal for Japanese Application No. 2020-523030, mailed on Dec. 21, 2021, 10 pages.
Notice of Reasons for Rejection for Japanese Application No. 2020-523030, mailed on Jul. 6, 2021, 11 pages.
Notice to File a Response mailed Feb. 24, 2022 for Korean Application No. 10-2020-7011674, 10 pages.
Office Action and Examination Search Report for Canadian Patent Application No. 3,079,623, mailed on Dec. 29, 2021, 6 pages.
Office Action and search report mailed Nov. 6, 2020 for Russian Application No. 2020114662, 13 pages.
Office Action for Canadian Application No. 3,079,626, mailed Jul. 5, 2021, 7 pages.
Office Action for Canadian Application No. 3083326 mailed on Jul. 5, 2021, 4 pages.
Office Action for Japanese Application No. 2019-231762, mailed on Dec. 15, 2020, 6 pages.
Office Action For Japanese Application No. 2020-526244, mailed on Jul. 13, 2021, 20 pages.
Office Action for Korean Application No. 10-2020-7011666, mailed on Dec. 20, 2021, 13 pages.
Office Action For Russian Application No. 2020114650, mailed on Nov. 20, 2020, 9 pages.
Office action for the JP application. 2019-560324 mailed on Jul. 28, 2020, 7 pages.
Office Action mailed Apr. 7, 2021 for Chilean Application No. 202001064, 13 pages.
Office Action mailed Apr. 14, 2022 for Russian Application No. 2021129125, 8 pages.
Office Action mailed Aug. 17, 2022 for Russian Application No. 2021129125, 12 pages.
Office Action mailed Aug. 23, 2021 for Chilean Application No. 202001064, 16 pages.
On Sep. 8, 2020, the applicant presented, in the European phase, a new specification amended, with only 16 clauses, with three independent claims—EP3614870, 6 pages.
Search Report for Japanese Application No. 2020-523030, mailed Jun. 30, 2021, 28 pages.
Search Report for Russian Application No. 2020114658 mailed on Nov. 12, 2020, 3 pages.
Search Report for Russian Application No. 2020116788 mailed on Dec. 21, 2020, 2 pages.
Smoke in Style, "Hybrid Electronic Pipe Kit," retrieved from https://www.smokeinstyle.com/hybrid-electronic-pipe-, on Mar. 3, 2021, 8 pages.
Wikipedia., "Academic Dictionary Definition of Cartridge," 2022, Retrieved from the Internet: https://dic.academic.ru/dic.nsf/ruwiki/195029, 6 pages.
Written Opinion for Application No. PCT/EP2018/079136, mailed on Feb. 12, 2019, 7 pages.
Written Opinion for Application No. PCT/EP2018/082411, mailed on Mar. 22, 2019, 5 pages.
Notice of Reasons for Rejection received for Japanese Patent Application No. 2021-068570, mailed on Dec. 20, 2022, 9 pages (4 pages of English Translation and 5 pages of Official Copy).
Office Action received for Chinese Patent Application No. 201880068511.3, mailed on Dec. 22, 2022, 14 pages (5 pages of English Translation and 9 pages of Official Copy).

\* cited by examiner

MOUTHPIECE ASSEMBLY

PRIORITY CLAIM

The present application is a National Phase entry of PCT Application No. PCT/EP2018/079137, filed Oct. 24, 2018, which claims priority from GB Patent Application No. 1717497.0, filed Oct. 24, 2017, each of which is hereby fully incorporated herein by reference.

TECHNICAL FIELD

The present disclosure relates to a mouthpiece assembly for an aerosol provision device for generating an inhalable medium.

BACKGROUND

Smoking articles such as cigarettes, cigars and the like burn tobacco during use to create tobacco smoke.

Attempts have been made to provide alternatives to these articles that burn tobacco by creating products that release compounds without burning.

Examples of such products are heating devices which release compounds by heating, but not burning, the material. The material may be for example tobacco or other non-tobacco products, which may or may not contain nicotine.

As another example, there are so-called e-cigarette devices. These devices contain an aerosolizable substance, typically a liquid, which is heated to be vaporized to produce an inhalable vapor or aerosol. The liquid may contain nicotine and/or flavorings and/or aerosol-generating substances, such as glycerol. Such known e-cigarette devices typically do not contain or use tobacco.

As yet another example, there are so-called hybrid devices. These hybrid devices typically contain separately an aerosolizable substance, again typically a liquid, and a container for a material. In typical examples the material may be tobacco or other flavor material. The liquid is aerosolized to produce an inhalable vapor or aerosol which passes through the container for a material so that a property, such as a flavor, is imparted to the vapor or aerosol by the material before being inhaled by a user.

In a hybrid device, the aerosolizable material may be provided in a cartridge, typically a liquid cartridge. It may be desirable to be able to detach this cartridge from a body portion of the device, and some known hybrid devices allow a cartridge to be detached from a body portion in order to replace or refill the cartridge. For example, the cartridge may be replaced or refilled when the liquid in the cartridge is depleted, or when the user wishes to change the type of liquid being used in the device.

It is also known for the container for a material to be releasably attached to the device. This might be, typically, to replace the material when it is no longer having the desired effect on the aerosol passing through the chamber. It may also be when the user wishes to change the type of material used. The user may then supply a new container with fresh material, or a different material, or the container may be refilled with a material and reattached to the device. Alternatively, in known devices, the container may not be attachable from the device and may be refilled with material while remaining attached to the device.

It is often the case that it is desirable to replace the material more frequently than the cartridge. A reason for this, among others, is that the container is often smaller than a liquid reservoir of the cartridge, and the volume of material held in the container may be less than the volume of liquid held in the cartridge. It is then desirable to be able to detach a container for a material from the hybrid device while leaving the liquid cartridge attached to the body portion of the device. In a typical hybrid device with a releasably attached material container, the container, being downstream of the liquid cartridge, is releasably attached to the cartridge, rather than to any other part of the device.

SUMMARY

According to a first aspect of the present disclosure, there is provided a mouthpiece assembly for an aerosol provision device, the mouthpiece assembly comprising: a first housing for being received, in use, in a mouth of a user; a second housing for containing a material through which, in use, an aerosol generated by the aerosol provision device flows before passing out of the mouthpiece assembly for inhalation by the user; and wherein the first housing and the second housing are connected together to form the mouthpiece assembly and the mouthpiece assembly is configured to be releasably connectable to a section of the aerosol provision device.

The mouthpiece assembly may comprise at least a first barrier that is porous to the flow of aerosol and which prevents material in the second housing from exiting the second housing.

The first barrier may be arranged towards a first opening at a proximal end of the second housing.

The mouthpiece assembly may comprise a second barrier that is porous to the flow of aerosol and which prevents material in the second housing from exiting the second housing, wherein the second barrier is arranged towards a second opening at a distal end of the second housing.

The second housing may be a tube and wherein first opening is at the proximal end of the tube and the second opening is at the distal end of the tube.

The second housing may comprise a first portion that is within the first housing and a second portion that extends out of the first housing, wherein the second portion is within the aerosol provision device when the mouthpiece assembly is connected to the section of the aerosol provision device.

The mouthpiece assembly may be configured to be releasably connected to the section of the aerosol provision device via a push fit connection.

The mouthpiece assembly may comprise at least one first surface formation which is configured to interface with an inner surface of the section of the aerosol provision device.

At least one of the at least one first surface formations may be configured to interact with a corresponding second surface formation on the inner surface of the section of the aerosol provision system.

According to a second aspect of the disclosure there is provided a method of manufacturing a mouthpiece assembly according to the first aspect, the method comprising: providing the first housing; providing the second housing; providing the material into the second housing; and connecting the first housing and the second housing.

Connecting the first housing and the second housing may comprise push-fitting.

Attaching the first housing and the second housing may comprise applying adhesive between contacting surfaces of the first housing and the second housing.

Attaching the first housing and the second housing may comprise ultrasonic welding.

According to a third aspect of the disclosure there is provided an aerosol provision device comprising a mouthpiece assembly according to the first aspect and a device body.

The device may further comprise a cartridge, wherein the mouthpiece assembly is releasably connected to the cartridge.

BRIEF DESCRIPTION OF THE DRAWINGS

Embodiments of the disclosure will now be described, by way of example only, with reference to the accompanying drawings, in which.

DETAILED DESCRIPTION

Figure 1:
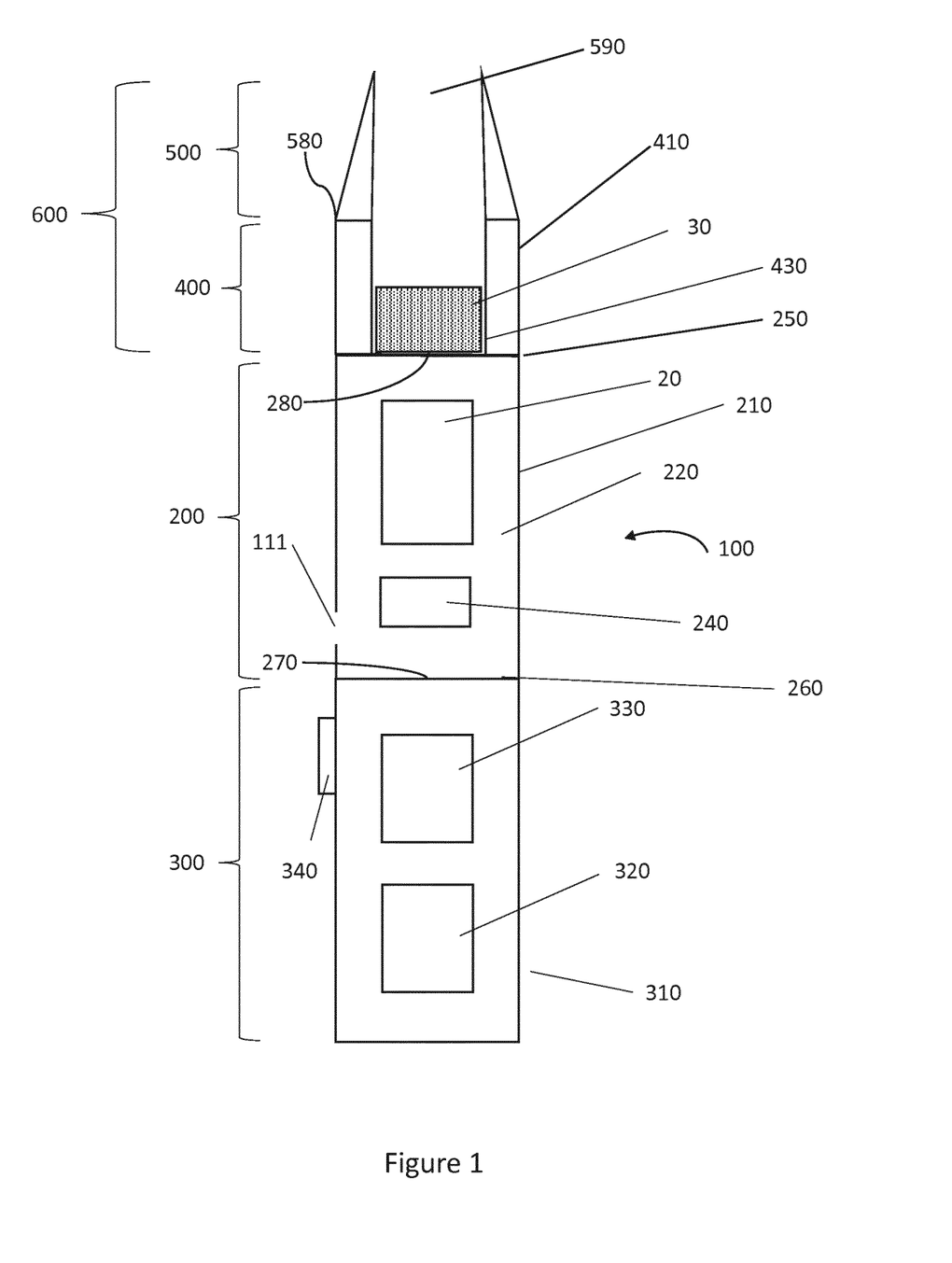
FIG. 1 shows a schematic longitudinal cross-sectional illustration of an aerosol provision device for generating an inhalable medium, wherein the device is shown in a vertical orientation.

Referring to FIG. 1, a schematic of an aerosol provision device 100 is illustrated. The aerosol provision device 100 is an inhalation device (i.e. a user uses it to inhale an aerosol provided by the system 100) and the device 100 is a hand-held device. In this example, the device 100 is an electronic device.

In broad outline, the device 100 volatilizes an aerosol provision material 20 provided in a cartridge 200. In this example the aerosol provision material 20 is a liquid, for example, an e-cigarette liquid, however in other examples the aerosol provision material may any other type of aerosolizable material, such as a gel. The device 100 in the example is a so-called hybrid device since any aerosol and/or vapor produced from the cartridge 200 passes through a material chamber 430 for containing a material 30 before being inhaled by a user.

The material 30 may impart to or modify a property, for example the flavor, of the vapor and/or aerosol before the vapor and/or aerosol passes out of the device 100 for inhalation by a user. The material 30 may, for example, consist of or comprise tobacco. As the aerosol passes through and over the material 30, for example tobacco, the aerosol entrains organic and other compounds or constituents from the material 30 that lend the material 30, for example tobacco, its organoleptic properties, thus imparting the flavor of the material 30 to the aerosol as it passes through the material chamber 430.

Suitable examples of the material 30 may comprise tobacco per se, different varieties of tobacco, tobacco derivatives, expanded tobacco, reconstituted tobacco, ground tobacco, tobacco extract, homogenized tobacco or tobacco substitutes. In the case of tobacco, the material 30, etc. may be in the form of a rod of tobacco, a pod or plug of tobacco, loose tobacco, agglomerates, etc., and may be in relatively dry form or in relatively moist form for example. The material 30 may be in the form of a plug of tobacco rod which is cut to length and placed into the material chamber 430. The material 30 may include other, non-tobacco, products, which, depending on the product, may or may not contain nicotine.

The material 30 may be for modifying a property of the aerosol other than (or in addition) to flavor.

In some examples, the material 30 may be or include a substance that modifies one or more other organoleptic properties of the aerosol (e.g. modifying the feel or smell or look of the aerosol to the user).

In some examples, the material 30 may be or include a substance that modifies the PH of the aerosol by either lowering or raising the PH (e.g. modifying the acidity or the basicity of the aerosol).

In some examples, the material 30 may be or include a substance that modifies (e.g. reduces) the amount of aldehydes in the aerosol.

In some examples, the material 30 may be or include a substance that modifies different combinations of two or more of these or indeed other properties of the aerosol flow.

It will be understood however that materials other than tobacco may be used to impart different flavors to the aerosol.

If the material 30 is or includes tobacco, it may be that the aerosol flow draws sufficient nicotine from the material 30. Alternatively or additionally, if the material 30 does not contain any tobacco, the material 30 may be enhanced with nicotine, for example by coating the material with nicotine. Indeed, even in the case that the material 30 is or includes tobacco, the material 30 may be coated or otherwise enhanced with nicotine. As another example, whether or not the material 30 is or includes tobacco and/or includes nicotine, nicotine may be provided in the aerosol provision material, in this example liquid 20. Accordingly, where it is intended that the system 100 provides nicotine for the user, the nicotine may be provided in the aerosol provision material 20, may be obtained from the material 30 in the case that the material is or includes tobacco, may be provided as a coating or the like on the material 30 if it is non-tobacco material, may be provided as a coating or the like on the material 30 if it is tobacco material, or any combination of these. Likewise, flavorings may be added to the material 30 (whether or not the substance is or includes tobacco) and/or to the aerosol provision material.

In at least some examples a vapor is produced that then at least partly condenses to form an aerosol before exiting the aerosol provision device 100 through the material chamber 430 for inhalation by a user (not shown).

In this respect, first it may be noted that, in general, a vapor is a substance in the gas phase at a temperature lower than its critical temperature, which means that for example the vapor can be condensed to a liquid by increasing its pressure without reducing the temperature. On the other hand, in general, an aerosol is a colloid of fine solid particles or liquid droplets, in air or another gas. A "colloid" is a substance in which microscopically dispersed insoluble particles are suspended throughout another substance.

For reasons of convenience, as used herein the term aerosol should be taken as meaning an aerosol, a vapor or a combination of an aerosol and vapor.

Returning to FIG. 1, the device 100 of this example comprises a cartridge 200, a body portion 300, and a mouthpiece assembly 600. The mouthpiece assembly 600 comprises a first housing 500, which is a mouthpiece for being received in the mouth of a user, and a second housing 400 which is for containing a material 30. The first housing 500 will be referred to herein as a mouthpiece, while the second housing 400 will be referred to as a container.

The cartridge 200 is for containing aerosol provision material 20, which in this case, as mentioned above, is e-liquid, while the body portion 300 is for powering and controlling the device 100.

The cartridge 200 comprises a third "upper" housing 210 and the body portion 300 comprises a fourth "lower" housing 310. The upper housing 210 is releasably attached to the lower housing 310 through a first connector arrangement 270. The first connector arrangement 270 is discussed in more detail below.

The cartridge 200 comprises a liquid reservoir 220 for containing the e-liquid. The material container 400 comprises a chamber 430 for receiving a material 30. The material may comprise tobacco, or may not comprise tobacco.

In the example of FIG. 1, the cartridge 200 also contains a heating arrangement 240. The heating arrangement is for heating e-cigarette liquid 20 from the liquid reservoir 220 to generate a flow of aerosol (not shown).

The heating arrangement 240 may comprise at least one heating element (not shown). While the liquid reservoir 220 is shown above the heating arrangement 240 in FIG. 1, the liquid reservoir 220 may comprise an annular chamber (not shown) surrounding a central aperture (not shown) through which generated aerosol flows. The heating arrangement 240 may then comprise at least one wick (not shown) for supplying liquid 20 from the liquid reservoir 220 to the at least one heating element.

The heating arrangement 240 may be referred to as an "atomizer", and where the liquid cartridge 200 comprises an atomizer, the cartridge may be referred to as a "cartomizer." Alternatively to comprising a heating arrangement 240, the device may aerosolize liquid via non-heating means, such as via an ultrasonic atomizer.

The material 30, such as tobacco, can be heated by heat transfer from the aerosol flow to the material. In use, and particularly in the case that the material is tobacco, the tobacco, or at least the surface of the tobacco, can be heated to a temperature of between around 120° C. to 170° C., for example around 150° C., so as to ensure that an adequate or appropriate amount of the compounds are released from the tobacco. The amount of tobacco present may be for example in the range 100 to 400 mg or so. A most suitable value for the amount of tobacco may be for example in the range 150 to 380 mg which may found to be particularly suitable in some applications such as when the tobacco used in pH treated tobacco. In another example, a most suitable value for the amount of tobacco may be for example in the range 120 to 190 mg which may be found to be particularly suitable when ground tobacco is used. In a typical example, the amount of tobacco that is heated per operation of the system (i.e. per puff) may be in the corresponding range of around 8 to 50 mg.

The liquid 20 can be a liquid that is volatilizable at reasonable temperatures, such as in the range of 100–300° C. or more particularly around 150-250° C., as that helps to keep down the power consumption of the system 100. Suitable materials include those conventionally used in e-cigarette devices, including for example propylene glycol and glycerol (also known as glycerine).

The lower housing 310 contains a power source 320, typically a battery, which is electrically connected to various components of the device 100, including the heating arrangement 240.

The battery 320 may be a rechargeable battery or a disposable battery. A controller 330, which may comprise a micro-chip and associated circuitry is also provided in the second housing 310 for controlling the operation of various components of the device 100. A user input means 340, for example one or more control buttons, may be provided on the exterior of the second housing 310 for a user to operate the controller 330.

Accordingly, in use, a user draws on the mouthpiece 500, and air is drawn through one or more air inlets 111. The heater arrangement 240 is powered by the user operating the control button 340 (or alternatively by a puff detector (not shown), as is known per se) and liquid 20 drawn from the liquid reservoir 220 is heated by the heater arrangement 240 to volatilize the liquid 20 to generate aerosol which mixes with air flowing from the air inlet 111 to produce a flow of aerosol. The flow of aerosol is drawn through the material 30 in the chamber 430 and then out of the device 100 through an aperture 590 in the mouthpiece 500 for inhalation by the user. As the aerosol flow passes through the material 30, one or more components of the material 30 become entrained in the aerosol flow which may alter, or add to, a property of the aerosol, such as its taste.

The upper housing 210 has a distal end, or base end, 260 and a proximal end, or mouth end, 250. As mentioned above, the cartridge 200 comprises the liquid reservoir 220 which may take various different forms. In one example, the liquid reservoir 220 is in the form of an annular chamber which extends axially in the first housing 210 between the proximal end 250 and the base end 260. The distal end 260 of the cartridge 200 comprises a first connector arrangement 270 for releasably attaching the cartridge housing 210 to the body portion housing 310. At a proximal end, or mouth end, 250 of the cartridge 200, the cartridge comprises a second connector arrangement 280 which releasably connects the cartridge 200 to the material container 400 by releasably connecting the cartridge housing 210 to a material container housing 410. The first connector arrangement 270 and second connector arrangement 280 will be discussed in more detail below.

In some examples, it may be that the user only needs to top up or replace the material 30 from time to time, with sufficient liquid 20 being provided for several uses. In the example of FIG. 1, the cartridge 200 is releasably attached to the body portion 300, and once the liquid 20 has been consumed, the user disposes of the cartridge 200 and provides a new cartridge. In other examples, the cartridge 200 is not designed to be disposable and instead the user only needs to top up or replace the liquid 20 from time to time. In other examples, the cartridge 200 and the device body portion 300 are integrated in a single device and are not arranged to be detachable from each other. In such examples, the device may comprise a replaceable atomizer or replaceable heating means for producing aerosol from the aerosolizable substance.

The mouthpiece 500 in the example of FIG. 1 is shown connected to the material container 400 by a first attachment 580 to form a mouthpiece assembly 600. The first attachment 580 may be a releasable attachment, or alternatively, the mouthpiece 500 and the container 400 may be attached non-releasably, for example by ultrasonic welding or by an adhesive. Examples of the mouthpiece assembly will be discussed below with reference to FIGS. 4a and 4b, FIGS. 6a and 6b and FIG. 7.

Figure 2:
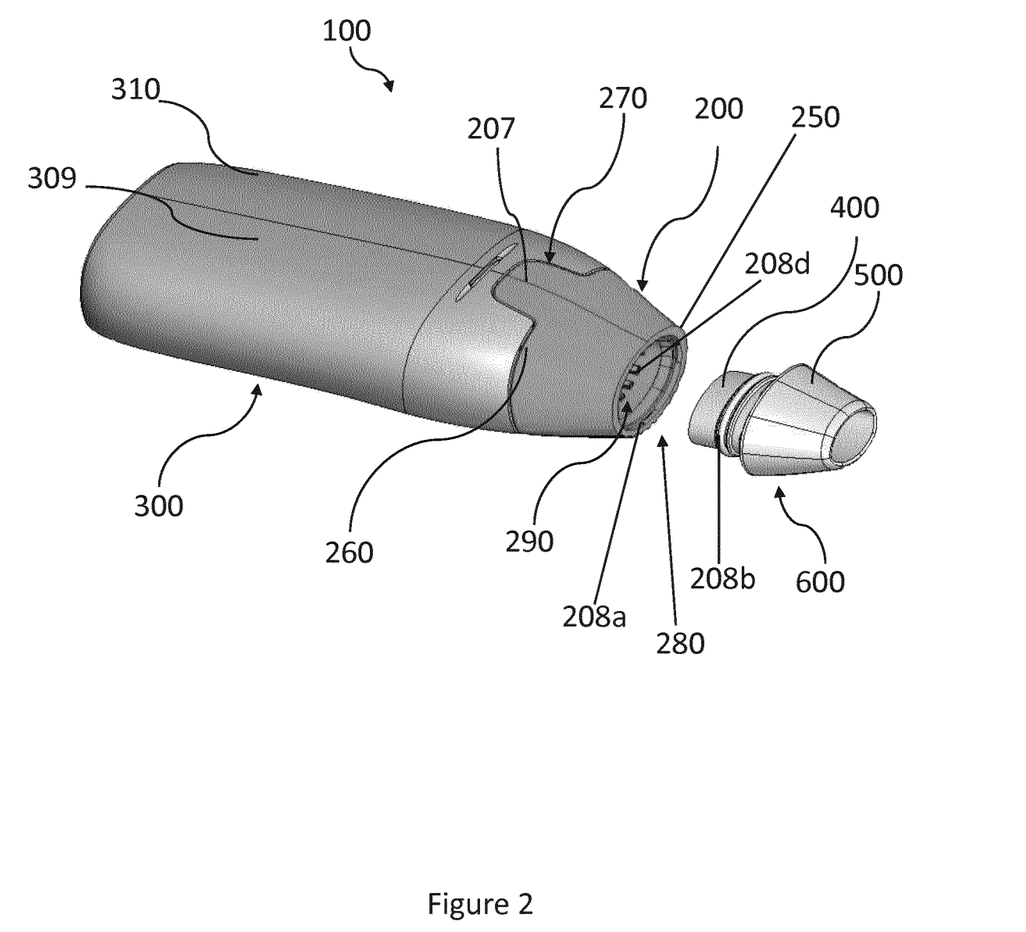
FIG. 2 shows a perspective view of an example of the device of FIG. 1, wherein the device is shown in a horizontal orientation with a mouthpiece assembly detached from the rest of the device.]

Referring now to FIG. 2, a perspective view of the example aerosol provision device 100 of FIG. 1 is shown. The aerosol provision device comprises the body portion 300, the e-liquid cartridge 200, and the mouthpiece assembly 600 comprising a material container 400. In this example, the material container 400 is contains tobacco, but a non-tobacco material, such as any of the materials listed above, may additionally or alternatively be contained within the chamber 430 of the container 400.

First Connector Arrangement

The cartridge 200 in this example comprises a first connector arrangement 270 for releasably attaching the cartridge 200 to the body portion 300. The first connector arrangement 270 may be configured in a locked state, wherein it is not possible for a user to detach the cartridge 200 from the device body 100, or the first connector arrangement may be configured in an unlocked state, wherein a user can detach the cartridge 200 from the device body by pulling the cartridge 200 and body portion 300 apart. When the first connector arrangement 270 is configured in the locked state the cartridge and body portion may not be separated by pulling. The first connector arrangement 270 can be configured in the unlocked configuration while the cartridge remains stationary with respect to the body portion. That is, the cartridge does not have to be rotated or otherwise moved to unlock the first connector arrangement 270.

For example, the first connector arrangement 270 may comprise a first element 207 on the cartridge 200 which interacts with a corresponding second element (not shown) on the body portion 300 when the first connector arrangement is in the locked configuration. The first connector arrangement 270 can be released by moving the first element 207 with respect to the second element while the cartridge 200 remains stationary with respect to the body portion 300. Here, it may be the first element 207 which is moved while the second element (not shown) remains stationary with respect to the body portion 300, it may be the second element which is moved while the first element remains stationary, or both the first and second elements may be moved with respect to the body portion.

Figure 3:
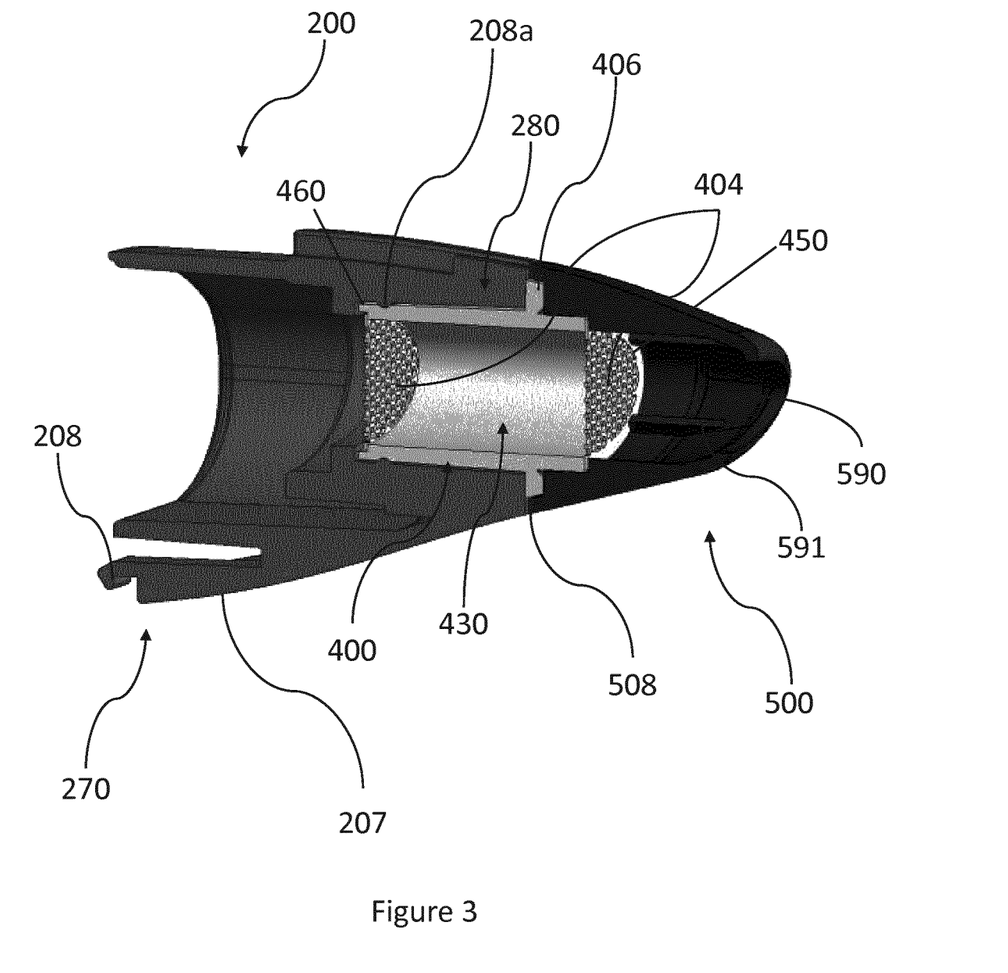
FIG. 3 shows a first example of a cartridge attached to a mouthpiece assembly.
Figure 5:
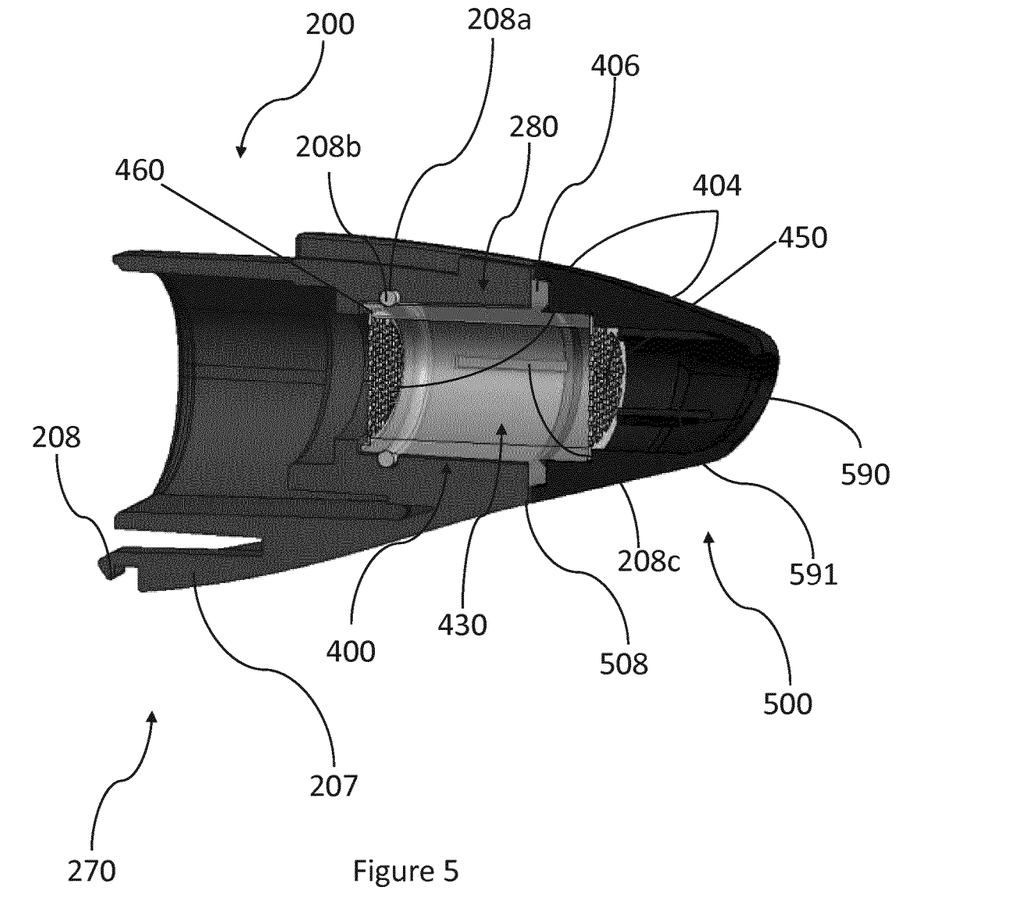
FIG. 5 shows a second example of a cartridge attached to a mouthpiece assembly.

In the example of FIG. 2, FIG. 3 and FIG. 5, the first connector arrangement 270 is a clip. To remove the cartridge 200 from the body portion 300 the clip 270 is configured in the unlocked configuration by moving the first element, a tab 207, with respect to a second element, a detent (not shown) on the body portion while the cartridge 200 remains stationary with respect to the body portion 300. The cartridge 200 can then be pulled free of the body portion 300.

The first connector arrangement 270 can thus be rapidly configured from being in the locked configuration to being in the unlocked configuration without having to rotate or otherwise move the cartridge with respect to the device body, such as would be the case where a cartridge is screw-fit to a device body. Additionally, in the examples of FIGS. 2 and 3, the first connector arrangement 270 automatically enters the locked configuration when the cartridge 200 is pushed together with the device body 300 with their longitudinal axes suitably aligned. That is, the clip 207 automatically snaps into the locked configuration, providing for the cartridge and device body to be rapidly attached, again not requiring screwing together of any components.

The example first connector arrangement 270 of FIG. 2, FIG. 3 and FIG. 5 has one tab, a first tab 207, which interfaces with a respective detent (not shown) in the body portion 300. In other examples, the first connector arrangement 270 may comprise a plurality of tabs and may comprise two, three, four, five or more tabs situated at any point around the circumference of the distal end 260 of the cartridge. In another advantageous example, the clip 270 has two tabs which are advantageously situated on opposite sides of the distal end 260 of the cartridge 200. Each tab 207 may be flexible and may be formed of a flexible plastics material.

The cartridge 200 in the example of FIG. 2 is shaped with a proximal end 250 having a smaller cross-sectional area than a distal end 260.

When the cartridge 200 and body portion 300 are attached with the clip 270 in the locked configuration, the cartridge 200 makes the necessary electrical connections with the body portion such that power is supplied to the cartridge 200. The device 100 is shown in FIG. 2 with the clip 270 in this locked configuration.

In order to release the cartridge 200 from the body portion 300 the first connector arrangement 270 must be configured in an unlocked state. In the example of FIG. 2 and FIG. 3, to configure the first connector arrangement in an unlocked state the user presses the first tab 207 radially inwards, towards the longitudinal axis of the device 100.

Now with reference to FIG. 3 (the first connector arrangement of FIG. 5 also comprises the same features now to be described), an example first tab 207 is shown comprising a hooked portion 208 at the distal end of the first tab 207. The first tab 207 is flexible and is biased to the position in which it is shown. The hooked portion 208 becomes hooked in a detent (not shown) in the body portion 300 when in the locked configuration, preventing the cartridge 200 being pulled free of the body portion 300. When a user presses radially inwards on the first tab 207 the tab flexes radially inwards and frees the hooked portion 208 from the detent in the body portion 300. The clip 270 thereby enters an unlocked configuration. The user may then detach the cartridge 200 from the body portion 300 by pulling the cartridge and the body portion apart while keeping tab 207 depressed (and thus keeping the first connector arrangement 270 in the unlocked configuration).

In other examples comprising more than one tab 207, each tab may interacts with a respective detent and may be released in the same way as described for the first tab 207 such that a user must keep all tabs depressed to configure the first connector arrangement 270 in the unlocked state.

In other examples not shown, the first connector arrangement may comprise a release button which a user presses to configure the first connector arrangement in the unlocked configuration.

Providing a first connector arrangement which is in a locked state by default but which may be unlocked by pressing and detached by pulling, such as in the example of FIG. 2, provides a secure attachment while allowing for a user to quickly and easily detach a cartridge 200 from the device body 300.

Second Connector Arrangement

The cartridge 200 also comprises a second connector arrangement 280, through which the mouthpiece assembly 600, comprising material container 400, may be attached to the cartridge 200. The second connector arrangement 280 is advantageously an arrangement that allows the mouthpiece assembly 600 to be push-fit to the cartridge 200.

That is, advantageously, as in the examples shown in FIGS. 2 to 7, the second connector arrangement 280 is a push-fit attachment which allows the user to separate the mouthpiece assembly 600 from the cartridge 200 by pulling the two apart. This provides for quick and easy detachment of the mouthpiece assembly 600 from the device 100, for example when the user wishes to replace the material container.

In FIG. 2, FIG. 3, and FIG. 5, examples of the second connector arrangement 280 are shown, comprising a recess 290 at the proximal end 250 of the cartridge 200 for accommodating a portion of the mouthpiece assembly 600. To attach to a mouthpiece assembly 600, the container 400 is inserted into the recess 290 and a portion of the container 400 is held in the recess 290 by friction or snap-fitting.

In advantageous examples the material container 400 comprises at least one first surface formation 208b, 208c, on its outer surface which interacts via friction with a corresponding at least one second surface formation 208a, 208d on an inner surface of the recess 290.

The at least one first surface formation 208b, 208c on the surface of the container 400 interacts with the at least one second surface formation 208a, 208d on the inner surface of the recess 290 to form a substantially airtight seal around the container 400 when the container 400 is connected to the cartridge 200 via the second connector arrangement 280. In this way, the second connector arrangement 280 substantially prevents leakage of aerosol or loss of pressure from the device.

Each of the at least one first surface formation 208b, 208c may comprise at least one formation, such as a rib, protruding radially outwards from the surface of the container 400, and/or may comprise at least one depression, such as a groove, in the surface of the container 400. Similarly, the at least one second formation 208a, 208d on the inner surface of the recess 290 may comprise at least one formation protruding radially from the inner surface of the recess 290 and/or at least one depression in the inner surface of the recess 290.

In advantageous examples, interaction between the at least one first surface formation 208b, 208c and the at least one second surface formation 208a, 208d provides for the second releasable attachment 280 to provide for snap-fitting of the container 400 to the cartridge 200. In some examples (not shown), one of the at least one first surface formations may be a surface formation which is biased and which at least partially retracts when the container 400 is in the process of being connected to the cartridge 200 and snaps into interaction with a corresponding second surface formation, providing a substantially airtight seal, when the container 400 is inserted into the recess 290.

In other examples, such as the examples shown in FIG. 3 and FIG. 5, the tolerances of the dimensions of the container 400; the recess 290; and their respective surface formations; may be such that the surface formations need not be biased and the container 400 is held in place, and a substantially airtight seal made, by interactions between fixed surface formations (first surface formations 208b, 208c and second surface formations 208).

Figure 4A:
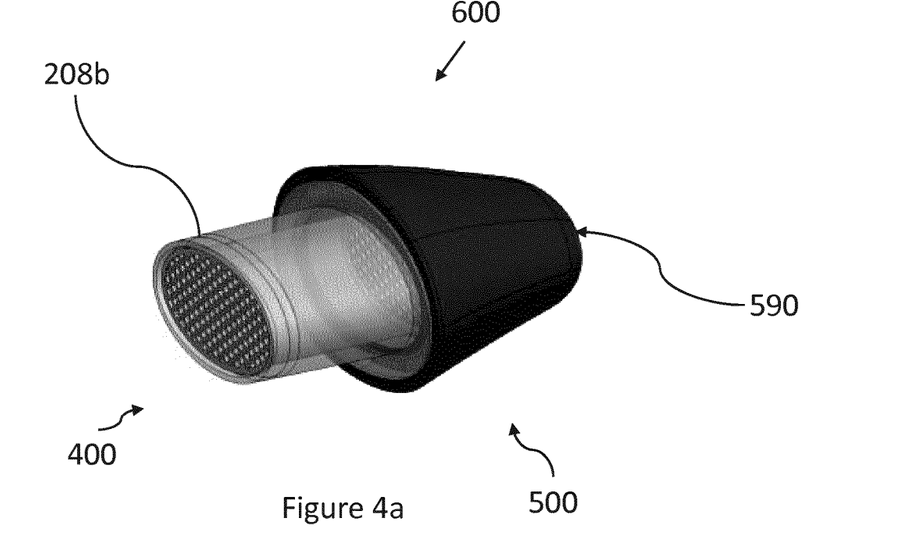
FIG. 4a shows a perspective view of a mouthpiece assembly, while FIG. 4b a perspective view of the same assembly with the mouthpiece detached in order to show details of the second housing.
Figure 4B:
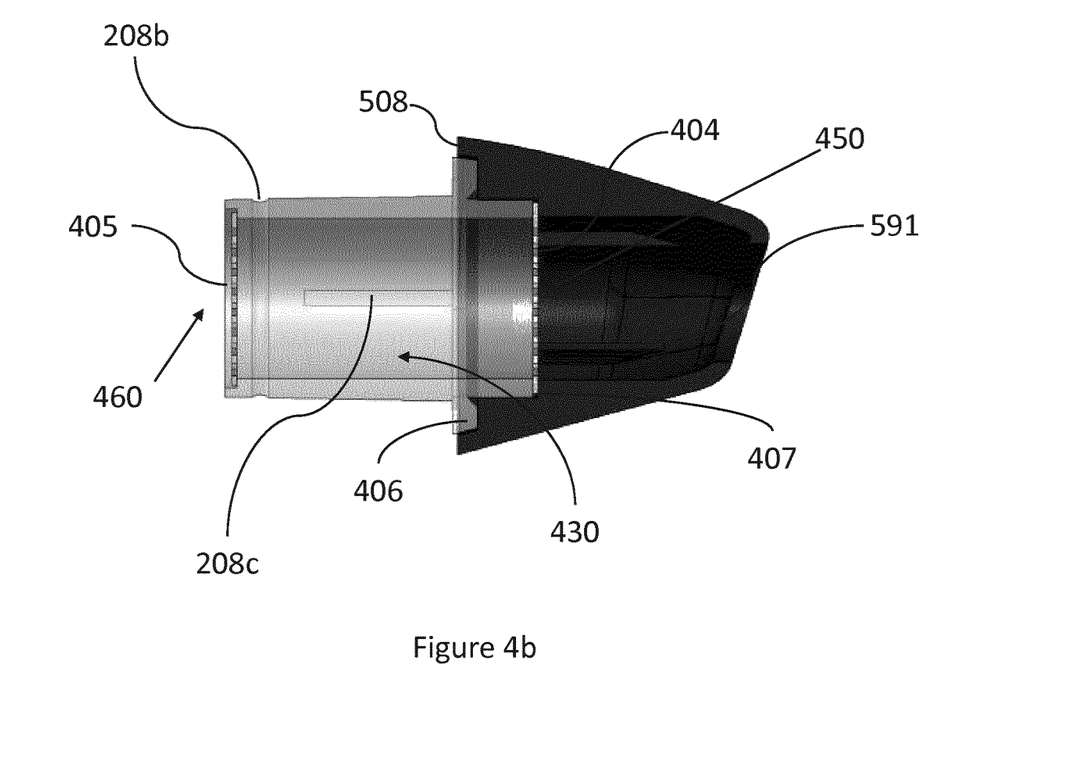

In the example of FIG. 3 and FIGS. 4a and 4b, the first surface formations on the surface of the container 400 comprise at least one groove 208b while the at least one second surface formation 208a of the recess 290 comprises at least one circumferential ridge 208a for interacting with the at least one groove 208b on the surface of the container 400. In this example, the groove 208b can have a width of between about 0.15 mm and about 0.17 mm. In the example of FIG. 4a and FIG. 4b, the surface of the container 400 comprises a longitudinal formation 208c, which may be a ridge or a groove, for interacting with a corresponding longitudinal formation (208d, FIG. 2) on the inner surface of the recess 290.

In contrast, in the example of FIG. 5, FIG. 6a and FIG. 6b, and FIG. 7, the first surface formations on the surface of the container 400 comprise at least one ridge 208b, 208c, for interacting with at least one groove 208a, 208d in the inner surface of the recess 290. The surface formations 208a, 208b, 208c in the example of FIGS. 5 to 7 will be discussed below in more detail.

As best seen in FIG. 2, when the first connector arrangement 270 of the cartridge 200 is configured in a locked state, wherein the cartridge cannot be separated from the body portion 300 by pulling unless a user presses the tab 207, inadvertent detaching of the cartridge from the device body can be avoided. That is, a user can easily separate the mouthpiece assembly 600 from the cartridge 200 by pulling, without separating the cartridge from the device body 300. With a device 100 such as in this example, the material 30 is often changed more frequently that the liquid 20; this arrangement makes replacement of the material 30 easier and more efficient.

Mouthpiece Assembly

An example of the mouthpiece assembly 600 will now be described in more detail with reference to FIG. 6a, FIG. 500 detached from the second, material container, housing 400 to provide a view of the proximal end 407 of the container 400.

The mouthpiece assembly 600 comprises a material container 400 and mouthpiece 500. As mentioned above, the container 400 comprises at least one first surface formation 208b, 208c, in this case a set of first ridges or ribs 208b, 208c on its outer surface for interacting via friction with the cartridge 200 into which the container 400 is fit in use.

Figure 6A:
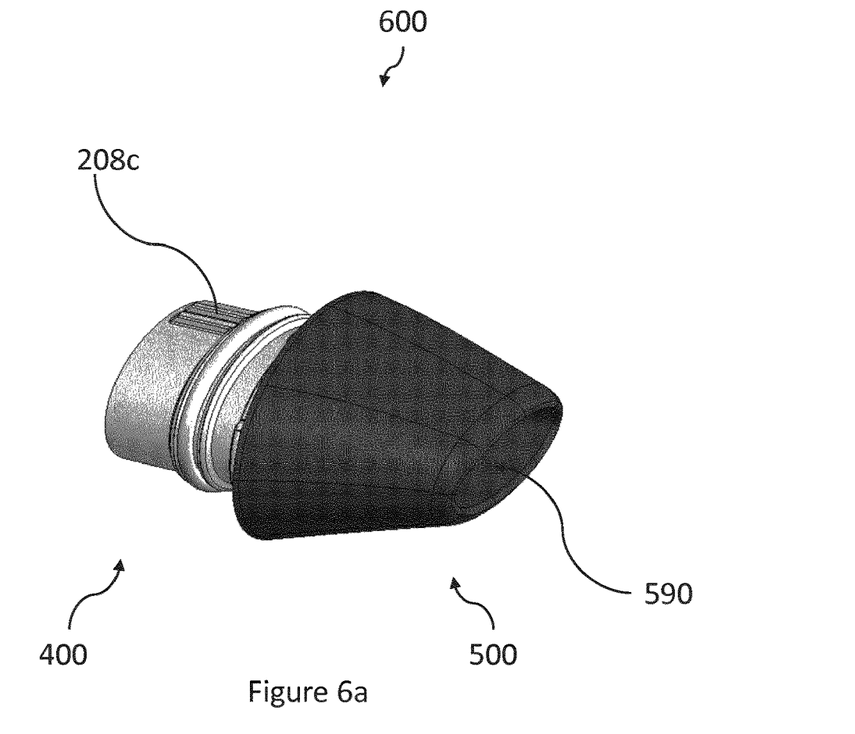
FIG. 6a shows a perspective view of a second example mouthpiece assembly, while FIG. 6b a perspective view of the second mouthpiece assembly with the mouthpiece detached in order to show details of the second housing.
Figure 6B:
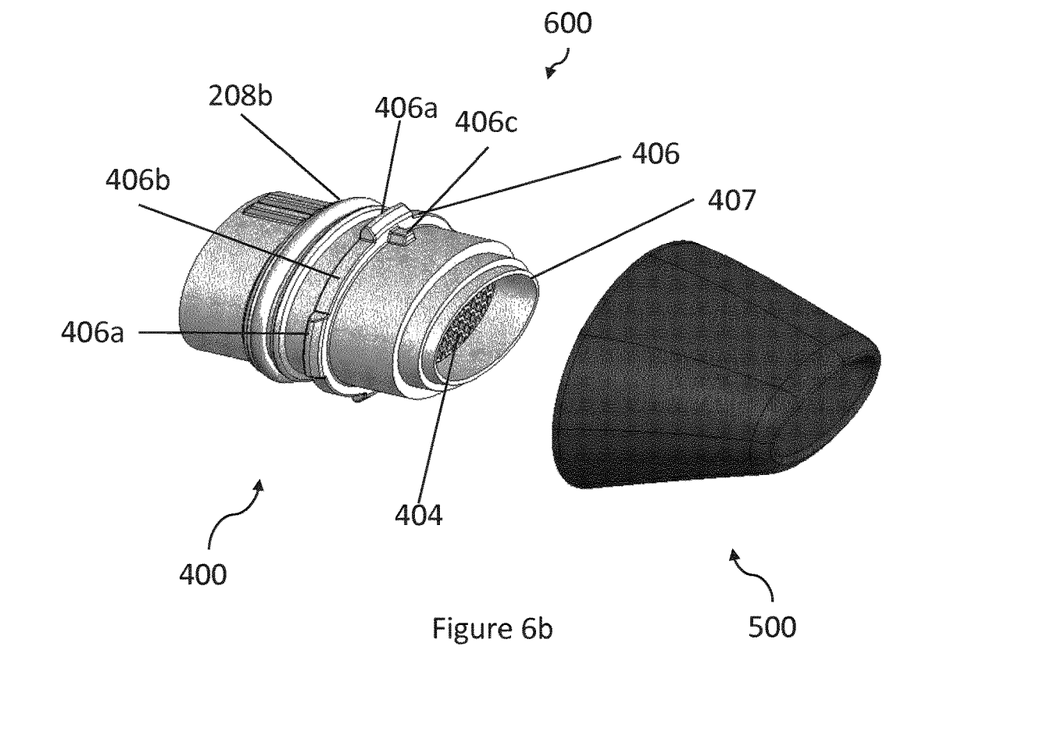
Figure 7:
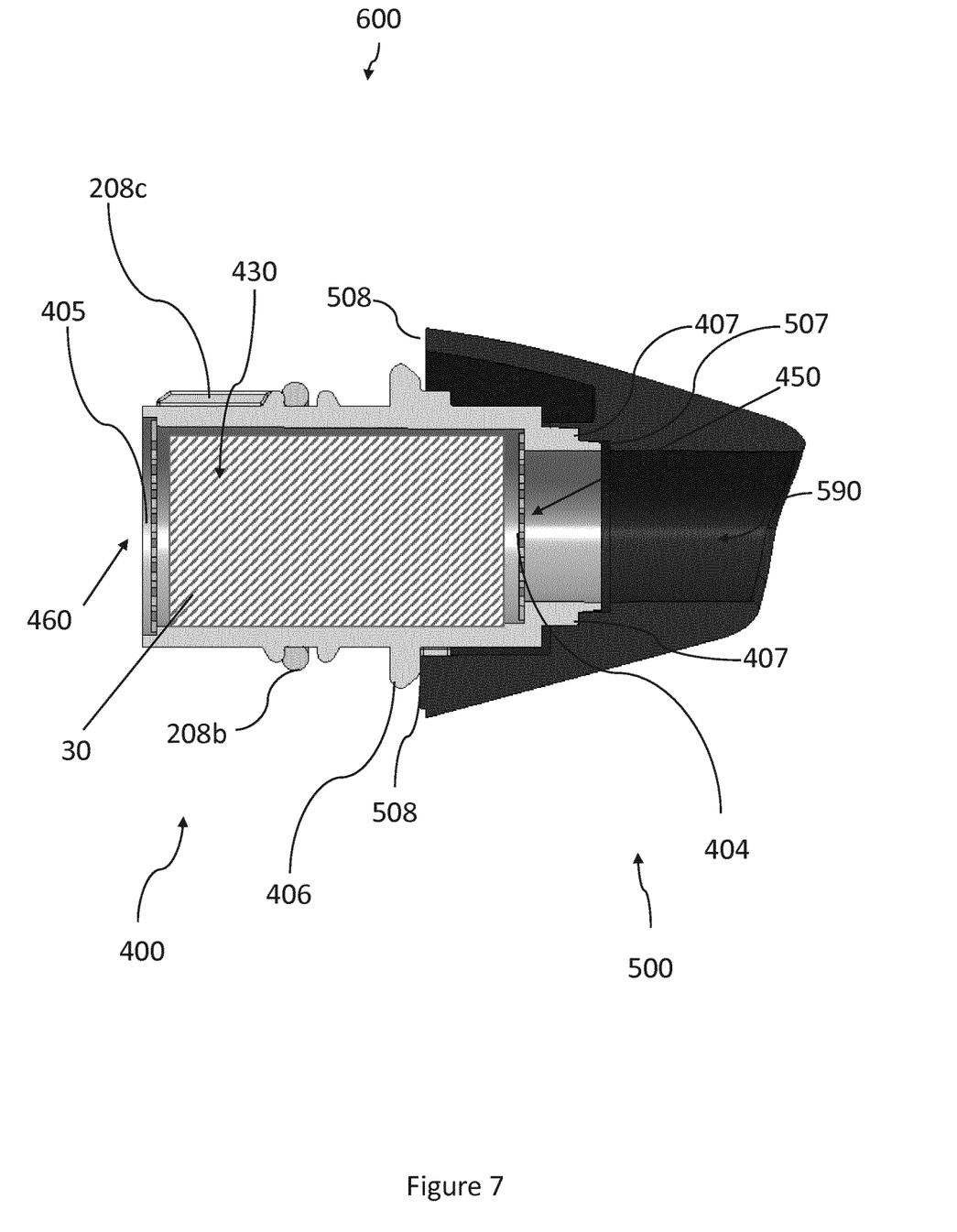
FIG. 7 shows a longitudinal cross-sectional view of the mouthpiece assembly of FIGS. 6a and 6b.

In the example of FIG. 6a, FIG. 6b and FIG. 7, first ridges 208b extend circumferentially around an outer surface of the container 400. The first ridges 208b, 208c, in this example also comprise one or more circumferential ridges 208b. Advantageously the container comprises two or more circumferential ridges 208b or three or more circumferential ridges 208b. In this example, as seen best in FIG. 6b, there are three circumferential ridges 208b, with one central circumferential ridge and two peripheral circumferential ridges. In this example, the central circumferential ridge extends further radially from the surface of the container 400 than the peripheral circumferential ridges extend radially from the surface of the container and the width of the central circumferential ridge can be between about 0.15 mm and about 0.17 mm.

In this example, the second surface formation 208a, 208d on the inner surface of recess 290 of the cartridge 200 may comprise at least one circumferential groove (208a FIG. 5) with which the first ridges 208b, 208c interact. Continuing with the example of FIG. 6a, FIG. 6b and FIG. 7, at least one of the first surface formations may be a rib 208b of flexible and/or compressible material, such as a rubber or a plastics material, for example silicone, which may compress to allow the material container 400 to be fitted into the recess 290 and expand to interact with a corresponding groove 208a in the surface of recess 290, thus holding the container 400 in place and contributing to forming a substantially airtight seal.

The set of first ridges of the example container 400 shown in FIG. 6a, FIG. 6b and FIG. 7 also comprises at least one longitudinal ridge 208c which extends along the surface of the container 400. In FIGS. 4a, 4b, it can be seen that the container 400 in this example comprises a plurality of longitudinal ridges 208c. The longitudinal ridges 208c may interact with the inner surface of the recess 290 and may interact with at least one corresponding longitudinal groove (208d, FIG. 2) on the inner surface of the recess 290. The longitudinal ridges 208c on the container 400 may assist with providing a substantially airtight seal and may additionally assist with achieving correct alignment between the container 400 and the cartridge 200 when the container 400 is being inserted into the recess 290. In other examples (not shown), the recess 290 may comprise a longitudinal ridge while the container 400 comprises a longitudinal groove.

The container 400 may comprise any number of ridges or grooves extending in any direction along its surface. In other examples, the container 400 may not comprise any surface formations and may be push-fit to the cartridge 200 purely by friction between the surfaces of the container and the recess 290 in the cartridge 200. The surface of the container 400 may comprise a material with a high coefficient of friction, such as a plastics or rubber material, to assist with friction-fitting. The container 400 may comprise a plastics material, such as polypropylene.

With reference to FIG. 7, the container 400 is shown to comprise a chamber 430 containing material 30. During manufacture, the container 400 is formed comprising a chamber 430 and a material 30 is then provided in the chamber. The material 30 is enclosed in the chamber by a first barrier 404 enclosing the chamber 430 near the proximal end 450 and a second barrier 405 enclosing the chamber 430 near the distal end 460.

The first barrier 404 and second barrier 405 comprise a mesh which is porous to the flow of aerosol and which prevents material 30, such as tobacco material, from exiting the chamber 430. The mesh is formed of a heat-resistant material, and is advantageously a heat-conductive material, such as a metal, since this aids in transferring heat to the material 30 in order to release more desired compounds from the material. The mesh being porous, allows aerosol to pass into the chamber 430 from the cartridge 200 at a distal end 460 and allows aerosol to pass out at a proximal end 450 into the inhalation aperture 590 for inhalation by a user. At the proximal end 250, the mesh prevents the material 30 from passing into the mouthpiece 500 and being inadvertently inhaled by a user.

In the case that the first barrier 404 and the second barrier 405 are both a mesh, the mesh may comprise a plastics material, such as polypropylene, or a metal, such as stainless steel or aluminum, and may comprise, for example, an aluminum foil. In some embodiments, the mesh is a stainless steel mesh. The mesh may have a thickness of between about 0.1 mm and about 1.2 mm and, for example, may have a thickness of around 1.2 mm when mesh comprises a plastics material; or a thickness of about 0.1 mm to about 0.3 mm when the mesh comprises a metal such as stainless steel; or a thickness of about 0.3 mm when the mesh comprises aluminum foil. The mesh is advantageously a mesh with a maximum aperture size which is advantageously smaller than the diameter of the material 30 to be contained. For example, where the material 30 is tobacco, the maximum mesh aperture size may be between about 0.2 mm and about 0.7 mm, and the maximum mesh aperture size may be chosen dependent on the type of tobacco used.

During construction, the first, mouthpiece housing 500 and the second, container, housing 400 are formed separately. The container 400 and the mouthpiece 500 are then attached to form the mouthpiece assembly 600.

The mouthpiece 500 may be formed, for example, from a plastics material, such as polypropylene, by injection molding. The shape of the mouthpiece 500 in the example of FIG. 7 is such that it is flared towards its distal end 508. This provides an ergonomic shape for a user's mouth to contact. In this example, at its distal end 508 the mouthpiece 500 has a diameter larger than the diameter of the proximal end of the cartridge 200. The mouthpiece 500 is formed such that it is configured to accommodate the material pod housing 409. The mouthpiece has an aperture 590 at its proximal end which may in some examples, such as that of FIG. 4b, comprise longitudinal fins 591 for channeling the flow of aerosol along the aperture 590.

The container 400 may also be formed from a plastics material by injection molding. The container 400 may for example be formed of polypropylene or of polyethylene terephthalate (PET). In this example, the proximal end 407 of the container comprises a step formation corresponding to a complementary shape of the interior surface 507 of the mouthpiece housing 500.

The container 400 further comprises a protrusion 406 which extends circumferentially around the surface of the container. This protrusion 406 is configured to abut with a distal end 508 of the mouthpiece housing 500 and further to provide a substantially airtight seal between the mouthpiece assembly 600 and the cartridge 200 when the two are fitted together via the second connector arrangement 280. The protrusion 406 may, in some examples such as the example of FIGS. 6a and 6b, comprise a plurality of substantially triangular prism portions 406a and a plurality of substantially flat portions 406b wherein a substantially flat portion 406b is located between each triangular prism portion 406a and the triangular prism portions 406a protrude a greater distance radially outwards than the flat portions 406b protrude radially outwards. The protrusion 406 in the example of FIGS. 6a and 6b also comprises at least one trapezoidal prism portion 406c, which is located adjacent a triangular prism portion 406a and is located further towards a proximal end 450 of the container 400. The planes of the non-parallel faces of the trapezoidal prism portion 406c are aligned along the longitudinal axis of the container 400. In attaching the mouthpiece 500 to the material pod 400, a portion of the container housing 400 is inserted into a recess at the distal end of the mouthpiece housing 500. When the container is inserted in this recess, the step formation at the proximal end 407 of the container 400 abuts against the interior surface 507 of the mouthpiece, and the distal end 508 of the mouthpiece 500 abuts against the protrusion 406.

Advantageously, the container housing 400 and mouthpiece housing 500 are attached via ultrasonic welding. The protrusion 406 then may provide the point of contact for an ultrasonic welding apparatus to attach the container 400 to the mouthpiece 500.

Alternatively, an adhesive at the points of contact (for example 407 and 507, and 406 and 508) may be used to attach the mouthpiece 500 to the material pod 400. In yet other alternatives, the mouthpiece 500 and container 400 may be releasably attached, for example via friction-fit or a snap-fit, in which case no adhesive is used.

In some examples the first mesh 404, and second mesh 405 is fitted to both the proximal end 450 and distal end 460 of the container 400 after the container 400 is formed and after the material 30 is provided in the chamber 430. In other examples, the first mesh 404 at either the proximal end 450 or the second mesh 405 at the distal end 460 of the container 400, advantageously the first mesh 404 at the proximal end 450, is formed integrally with the container 400. For example the first mesh 404 at the proximal end 450 may be formed during a process of molding the container 400 and material 30 may then be provided in the container before being enclosed by a second mesh 405 at the distal end 460.

In advantageous examples where the mouthpiece 500 and container 400 are joined by ultrasonic welding, the first mesh 404 is advantageously fitted to the proximal end 250 of the container 400 during the ultrasonic welding process.

Providing the container 400 and the mouthpiece 500 as a single mouthpiece assembly 600 provides ergonomic benefits to a user. For example, the user may grip and pull the mouthpiece 500 in order to remove the assembly 600 when the material 30 needs replacing. The user can then replace the assembly 600 as a whole, avoiding the time-consuming task of removing and replacing a material container which is separate from a mouthpiece. The assembly also ensures that a new mouthpiece is fitted with the same frequency that the material 30 needs replacing. This provides a hygiene benefit over mouthpieces in other devices which are used for more prolonged periods of time.

The mouthpiece assembly 600 also has benefits over hybrid devices which have a container which acts as a mouthpiece but which have no separate mouthpiece. Among other advantages, the mouthpiece assembly 600 provides an ergonomically shaped mouthpiece 500 and the flared shape reduces contact of the user's mouth with other parts of the device, thereby improving hygiene. Further, the inclusion of the mouthpiece 500 in addition to a material container 400 (as opposed to the container 400 acting as a contact point for a user's mouth) provides a spatial separation of the material pod from the user's mouth, preventing contact of the user with potentially hot material and reducing the likelihood that any of said material is inadvertently inhaled. The mouthpiece aperture 590 provides a space between the proximal end 450 of the container 400 and the proximal end of the mouthpiece aperture 590—this space may provide an improvement to the quality of aerosol flow delivered to a user. For example, the provision of this space may provide an improvement in any one of or any combination of the following properties of the aerosol flow delivered to a user: particle size in the aerosol; the degree of condensation of the aerosol from the aerosol flow; and the temperature of the aerosol flow.

As discussed above, the method of manufacturing the mouthpiece assembly 600 comprises: providing the container 400; providing a material 30 in the container; enclosing the material in the container with a first barrier; providing the mouthpiece 500; and attaching the container 400 to the mouthpiece 500. This is a cost-effective process resulting in an ergonomic and convenient product.

It should be noted that a number of other variations and alternatives to the examples described above are possible.

As an example, the material may be omitted from the material chamber, for example at the option of the user. This provides the user with more flexibility over the use of the cartridge as the user can use the cartridge as a classic "e-cigarette" device, only aerosolizing liquid and not having the aerosol pass over or through material, from time to time if they choose.

As used herein, the terms "flavor" and "flavorant" refer to materials which, where local regulations permit, may be used to create a desired taste or aroma in a product for adult consumers. They may include extracts (e.g., licorice, hydrangea, Japanese white bark magnolia leaf, chamomile, fenugreek, clove, menthol, Japanese mint, aniseed, cinnamon, herb, wintergreen, cherry, berry, peach, apple, Drambuie™, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, cassia, caraway, cognac, jasmine, ylang-ylang, sage, fennel, piment, ginger, anise, coriander, coffee, or a mint oil from any species of the genus Mentha), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, or powder.

In order to address various issues and advance the art, the entirety of this disclosure shows by way of illustration and example various embodiments in which the claimed invention may be practiced and which provide for a superior system arranged to generate an inhalable medium. The advantages and features of the disclosure are of a representative sample of embodiments only, and are not exhaustive and/or exclusive. They are presented only to assist in understanding and teach the claimed and otherwise disclosed features. It is to be understood that advantages, embodiments, examples, functions, features, structures and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist in essence of, various combinations of the disclosed elements, components, features, parts, steps, means, etc. The disclosure may include other inventions not presently claimed, but which may be claimed in future.

The invention claimed is:

1. A mouthpiece assembly for an aerosol provision device, the mouthpiece assembly comprising:
   a first housing for being received, in use, in a mouth of a user; and
   a second housing for containing a material, arranged such that, in use, an aerosol generated by the aerosol provision device enters the mouthpiece assembly and flows through the material in the second housing to be flavored by the material before passing out of the mouthpiece assembly for inhalation by the user;
   wherein the first housing and the second housing are connected together to form the mouthpiece assembly and the mouthpiece assembly is configured to be releasably connectable to a section of the aerosol provision device from which the aerosol generated by the aerosol provision device enters the mouthpiece assembly; and
   wherein the mouthpiece assembly is configured to be releasably connected to the section of the aerosol provision device via a push fit connection, and wherein the second housing is configured to be received in a recess in the section of the aerosol provision device and an outer circumferential surface of the second housing is configured to interface with an inner circumferential surface of the recess to provide the push fit connection
   wherein the outer circumferential surface of the second housing further comprises at least one first surface formation which is configured to interface with said inner circumferential surface of the recess.

2. The mouthpiece assembly according to claim 1, further comprising at least a first barrier that is porous to the flow of aerosol and which prevents material in the second housing from exiting the second housing.

3. The mouthpiece assembly according to claim 2, wherein the first barrier is arranged towards a first opening at a proximal end of the second housing.

4. The mouthpiece assembly according to claim 3, further comprising a second barrier that is porous to the flow of aerosol and which prevents material in the second housing from exiting the second housing, wherein the second barrier is arranged towards a second opening at a distal end of the second housing.

5. The mouthpiece assembly according to claim 4, wherein the second housing is a tube and the first opening is at the proximal end of the tube and the second opening is at the distal end of the tube.

6. The mouthpiece assembly according to claim 4, wherein the second barrier is a mesh.

7. The mouthpiece assembly according to claim 2, wherein the first barrier is a mesh.

8. The mouthpiece assembly according to claim 1, wherein the second housing comprises a first portion that is within the first housing and a second portion that extends out of the first housing and wherein the second portion is within the aerosol provision device when the mouthpiece assembly is connected to the section of the aerosol provision device.

9. The mouthpiece assembly according to claim 1, further comprising at least two first surface formations which are configured to interface with the inner surface of the section of the aerosol provision system.

10. The mouthpiece assembly according to claim 1, further comprising at least three first surface formations which are configured to interface with the inner surface of the section of the aerosol provision system.

11. The mouthpiece assembly according to claim 1, wherein at least one of the at least one first surface formations is a ridge that extends circumferentially around an outer surface of the second housing.

12. The mouthpiece assembly according to claim 1, wherein at least one of the at least one first surface formations is a ridge that extends longitudinally on an outer surface of the second housing.

13. The mouthpiece assembly according to claim 1, wherein at least one of the at least one first surface formations is configured to interact with a corresponding second surface formation on the inner surface of the section of the aerosol provision system.

14. The mouthpiece assembly according to claim 13, wherein the at least one of the first surface formations is a first ridge which is configured to interact with a corresponding second groove on the inner surface of the section of the aerosol provision system.

15. The mouthpiece assembly according to claim 13, wherein the at least one of the first surface formations is a second groove which is configured to interact with a corresponding second ridge on the inner surface of the section of the aerosol provision system.

16. The mouthpiece assembly according to claim 1, wherein the second housing comprises a protrusion against which a distal end of the first housing abuts.

17. The mouthpiece assembly according to claim 1, wherein the first housing comprises an aperture for the flow of aerosol to pass through for inhalation by the user and wherein the first housing is asymmetric about the aperture.

18. The mouthpiece assembly according to claim 1, wherein the first housing has a cross-sectional area at a distal end which is greater than cross-sectional area at a proximal end.

19. The mouthpiece assembly according to claim 1, wherein the first housing has a cross-sectional area at a distal end which is greater than a cross-sectional area of a proximal end of the second housing.

20. An aerosol provision device comprising a mouthpiece assembly according to claim 1 and a device body.

21. The aerosol provision device according to claim 20, wherein, when the mouthpiece assembly is connected to the device, at least a portion of the second housing is contained within the device.

22. The aerosol provision device according to claim 20, wherein the device further comprises a cartridge and wherein the mouthpiece assembly is releasably connected to the cartridge.

23. A method of manufacturing a mouthpiece assembly for an aerosol provision device, the mouthpiece assembly comprising a first housing for being received, in use, in a mouth of a user, and a second housing for containing a material, arranged such that, in use, an aerosol generated by the aerosol provision device enters the mouthpiece assembly and flows through the material in the second housing to be flavored by the material before passing out of the mouthpiece assembly for inhalation by the user, wherein the first housing and the second housing are connected together to form the mouthpiece assembly and the mouthpiece assembly is configured to be releasably connectable to a section of the aerosol provision device from which the aerosol generated by the aerosol provision device enters the mouthpiece assembly, the method comprising:

providing the first housing;

providing the second housing;

providing the material into the second housing; and connecting the first housing and the second housing.

24. The method according to claim 23, wherein connecting the first housing and the second housing comprises push-fitting.

25. The method according to claim 23, wherein attaching the first housing and the second housing comprises applying adhesive between contacting surfaces of the first housing and the second housing.

26. The method according to claim 23, wherein attaching the first housing and the second housing comprises ultrasonic welding.

27. The method according to claim 23, wherein providing the material within the second housing comprises enclosing at least a part of the second housing with a barrier which is porous to the flow of aerosol and which prevents material in the second housing from exiting the second housing.

* * * * *